United States Patent [19]
Herpers

[11] 4,407,287
[45] Oct. 4, 1983

[54] ATRIAL AND VENTRICULAR-ONLY PACEMAKER RESPONSIVE TO PREMATURE VENTRICULAR CONTRACTIONS

[75] Inventor: Lodewijk-Jozef Herpers, Kerkrade-West, Netherlands

[73] Assignee: Medtronic, Inc., Minneapolis, Minn.

[21] Appl. No.: 235,227

[22] Filed: Feb. 17, 1981

[51] Int. Cl.³ .............................................. A61N 1/38
[52] U.S. Cl. ................................................ 28/419 PG
[58] Field of Search ................................. 128/419 PG

[56] References Cited

U.S. PATENT DOCUMENTS

| 3,595,242 | 7/1971 | Berkovits | 128/419 PG |
| 3,648,707 | 3/1972 | Greatbatch | 128/419 PG |
| 3,661,158 | 5/1972 | Berkovits | 128/419 PG |
| 3,709,229 | 1/1973 | Berkovits | 128/419 PG |
| 3,759,266 | 9/1973 | Lee | 128/419 PG |
| 3,768,486 | 10/1973 | Berkovits | 128/419 PG |
| 3,903,897 | 9/1975 | Woollons | 128/419 PG |
| 4,059,116 | 11/1977 | Adams | 128/419 PG |
| 4,108,148 | 8/1978 | Cannon | 128/419 PG |

FOREIGN PATENT DOCUMENTS 2701104  1/1977  Fed. Rep. of Germany .

OTHER PUBLICATIONS

Irnich, Concept for an Optimum Pacemaker (Translation of Konzept Eines Optimal-Schrittmachers.
Rogel, The Universal Pacer, A Synchronized-Demand Pacemaker, Mar. 1971, pp. 466-471.
Hawthorne-Thalen, Boston Colloquim on Cardiac Pacing, 1977, pp. 111-122.

Primary Examiner—William E. Kamm
Attorney, Agent, or Firm—Joseph F. Breimayer; John L. Rooney; Robert C. Beck

[57] ABSTRACT

A programmable pacemaker pulse generator capable of operating in several atrial and ventricular pacing modes having atrial and ventricular sense amplifiers and output circuits and programmable memory and clock controlled digital timing circuits for selectively delivering stimulating pulses to the heart in an atrial synchronous mode of operation. The ventricular sense amplifier has a blanking and refractory period following the sensing of a ventricular heartbeat or the occurrence of a stimulation pulse. Delay means operatively connected to the atrial sense amplifier operate to trigger the generation of a ventricular stimulating pulse after an A-V delay interval following a sensed atrial depolarization. The A-V delay interval is lengthened by means responsive to the detection of two or more ventricular depolarizations without an intervening atrial depolarization, so as to avoid the application of a ventricular stimulating pulse into the vulnerable period (or T-wave) of the heart. In addition, the ventricular refractory period is prolonged by a like interval. In this way the time intervals are prolonged to alleviate the possibility of harmful pacing into the heart's vulnerable period while allowing the ventricular stimulating pulse to be delivered after the delay in synchrony with the detected P-wave.

12 Claims, 3 Drawing Figures

ATRIAL AND VENTRICULAR-ONLY PACEMAKER RESPONSIVE TO PREMATURE VENTRICULAR CONTRACTIONS

BACKGROUND OF THE INVENTION

1. Technical Field of the Invention

This invention pertains generally to the field of electrical heart pacemakers, and more specifically to improvements in atrial synchronous pacemakers or other pacemakers capable of operating in an atrial synchronous mode.

2. Description of the Prior Art

Atrial synchronous pacemakers are designed for use on patients whose hearts have normal atrial self pacing, but, due to a defect in the conduction from the atrium to the ventricle, the ventricles fail to beat or keep pace with the atrial rhythm. Atrial synchronous pacemakers are designed to sense the naturally occurring atrial contractions (depolarizations) and, at the end of a short time interval, to provide an electrical stimulation pulse to the ventricles of the heart so as to induce a ventricular contraction. The time delay interval is selected so that the atrial and ventricular contractions are synchronized with an appropriate delay interval for efficient pumping. Atrial synchronous pacing attempts to take the place of missing natural conduction of stimulating pulses from the atrium to the ventricle in the heart, while the heartbeat rate is free to follow, within limits, the natural rhythm established by the atrial self-pacing of the patient. Often other features are combined with atrial synchronous pacing, such as an upper rate limit, or reversion to fixed rate pacing if the spontaneous atrial rate drops below a predetermined rate. Also, provisions may be provided as is known in the art for programming the pacemaker after implantation to adjust the atrial-ventricular (A-V) delay, upper or lower rates, and other operating parameters. A ventricular inhibit function can also be provided so that if a ventricular depolarization does follow in response to an atrial depolarization, the ventricular depolarization will be sensed and the pacemaker will be inhibited from delivering a competitive ventricular stimulating pulse. In that manner, the stimulating pulses are delivered only if needed.

In addition to atrial synchronous pacemakers, other types of pacemakers capable of operating in a number of modes include atrial synchronous operation as one possible mode of operation. Dual sense-dual pace atrial-ventricular pacemakers, sometimes referred to as fully automatic pacemakers, are capable of selectively delivering stimulating pulses to both the atrium and the ventricle, and are also capable of sensing beats occurring in both chambers and operating as appropriate to maintain A-V synchrony. That type of fully automatic pacemaker will operate in an atrial synchronous mode if the patient's atrium is self pacing above the minimum rate (thus inhibiting delivery of atrial stimulation pulses) and if the ventricles are not contracting on their own at the proper time interval following the atrial contraction, thus resulting in atrial synchronous operation. Such a pulse generator is described in U.S. Pat. No. 4,312,355, by Hermann D. Funke and assigned to a subsidiary company of the assignee of the present invention.

Pacemakers operating in an atrial synchronous mode are subject to certain errors which, under certain circumstances, can lead to the delivery of a ventricular stimulating pulse at an inappropriate and possibly dangerous time period of the heartbeat cycle. The problem can occur when a premature ventricular contraction occurs prior to an atrial contraction. Although the atrial sense amplifier is intended to respond only to atrial depolarizations (P-waves) of the electrogram, in fact the R-waves from a ventricular depolarization may be sensed as a P-wave by the atrial sense amplifier. This starts the A-V delay interval, following which the pacemaker delivers a ventricular electrical stimulation pulse. This pulse may fall in time in the vulnerable period of the heart during repolarization from the premature ventricular contraction. Delivery of a stimulation pulse during this vulnerable period is medically unsound, because it could be dangerous to the patient under some circumstances, as it might cause fibrillation of the heart.

It has been recognized in the prior art that the above sequence of events beginning with a premature ventricular contraction and leading to delivery of a ventricular stimulation pulse during the vulnerable period is unacceptable, and various solutions have been proposed. Drug therapy has been used in conjunction with atrial-triggered synchronous ventricular pacemakers in an attempt to suppress premature ventricular contractions so that they would not be detected by the atrial sensing circuit. However, drug therapy has limitations and may be ineffective or inappropriate in certain circumstances and for certain patients. Electronic filtering has also been used in conjunction with the atrial sensing amplifier in order to discriminate the P-wave from the R-wave so as to reject the latter. However, filtration by itself is not workable or reliable in discriminating atrial from ventricular events, because of the inherent variabilities of the shape and frequency composition of R-waves and P-waves in the body. The R-wave in some individuals is more like the P-wave in other individuals, thus greatly complicating any attempt at discrimination by electronic filtering.

In U.S. Pat. No. 4,343,311 there is disclosed an atrial blanking overlap circuit and method for overcoming the above noted problem by sensing both in the atrium and ventricle and by using timing considerations to discriminate between P-waves and R-waves so that a stimulating ventricular pulse is delivered only in response to an actual atrial contraction and not in response to a premature ventricular contraction, when operating in atrial synchronous mode.

In my commonly assigned, copending U.S. patent application Ser. No. 235,232, filed Feb. 17, 1981, I further describe a circuit for prolonging the period of overlap in instances where the electrode repolarization voltages cause the sense amplifier output to be present at the end of a preset sampling period after the preceding R-wave. In such instances, the atrial and ventricular blanking periods, the ventricular refractory period and the upper rate intervals are all prolonged by the persistance of the sensed R-wave at the output of the sense amplifier.

The present invention overcomes a further problem arising from a ventricular depolarization or ectopic heart beat occuring prior to an expected atrial depolarization. In such cases, where the P-wave is sensed after the atrial blank interval (e.g. 160 ms) initiated by the ectopic R-wave, the P-wave may initiate the delivery of a ventricular output pulse after the A-V delay interval. The timing may be such that the ventricular stimulating pulse can be delivered into the vulnerable period. In the present invention, the A-V period is prolonged and the ventricular refractory period is lengthened in response to such a ventricular ectopic beat.

The invention is useful in both unipolar and bipolar pacemakers, and is particularly useful in unipolar pacemakers, because in the prior art it has been more difficult to discriminate P-waves from R-waves in the case of unipolar pacemakers. The preferred embodiment shown herein is for a unipolar pacemaker.

SUMMARY OF THE INVENTION

According to the present invention there is provided a pacemaker for selectively delivering stimulating pulses to the heart in an atrial synchronous mode of operation, including terminals for connection both to the ventricle and atrium of the patient's heart. Generating means are provided for selectively delivering ventricular electrical stimulation pulses through the ventricular terminal to the ventricle of the heart. A ventricular sense amplifier connects from the ventricular terminal and is operative for sensing ventricular beats of the heart. The ventricular sense amplifier has a blanking and refractory period following the sensing of a ventricular heartbeat or the occurrence of a stimulation pulse. An atrial sense amplifier is connected to the atrial terminal for sensing P-waves indicative of atrial depolarizations, and delay means operatively connected to the atrial sense amplifier operate to trigger the generation of a ventricular electrical stimulating pulse after a predetermined time interval following a sensed atrial depolarization. Control means are operatively associated with the atrial sense amplifier to render it inoperative during the refractory period of the ventricular sense amplifier, so that premature ventricular contractions or other ventricular events will not be erroneously detected by the atrial sense amplifier.

According to the present invention, the atrial-ventricular delay interval is lengthened by means responsive to the detection of two or more ventricular depolarizations without an intervening sensed atrial depolarization, so as to avoid the application of a ventricular stimulating pulse into the vulnerable period (or T-wave of the heart.)

In addition, the ventricular refractory period is prolonged by a like interval. In this way the time intervals are prolonged to alleviate the possibility of harmful pacing into the heart's vulnerable period while allowing the ventricular stimulating pulse to be delivered after the delay in synchrony with the detected P-wave.

The foregoing and additional advantages and characterizing features of the present invention will become clearly apparent upon reading of the ensuing detailed description of an illustrative embodiment thereof together with the included drawings depicting this theme.

DETAILED DESCRIPTION OF THE PREFERRED EMBODIMENT

Figure 1:
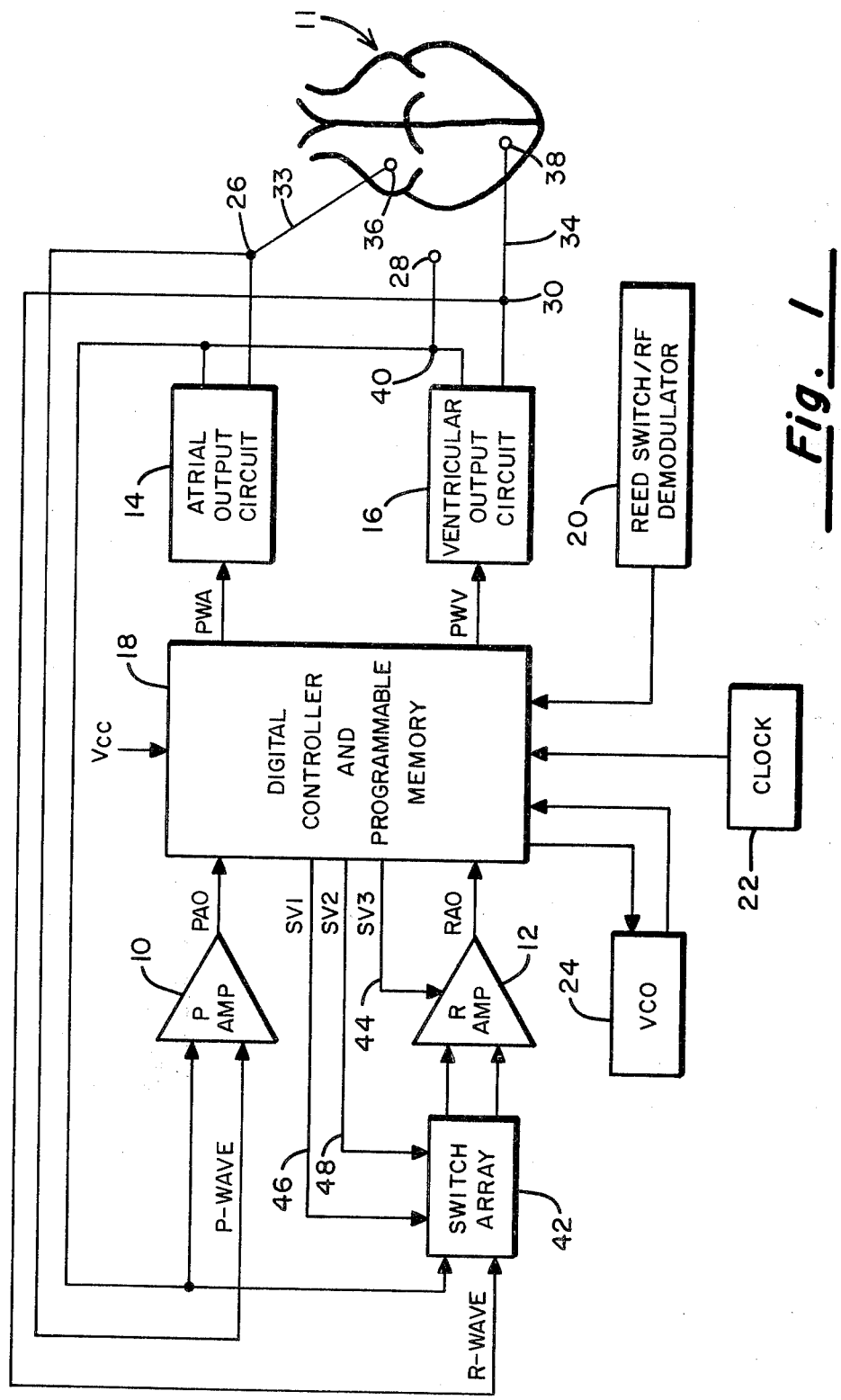
FIG. 1 is a block diagram of a heart pacemaker in which the present invention may be implemented.

In FIG. 1, the major functional elements of a pacemaker in which the present invention can be practised are shown in block diagram form. The pacemaker could either be external or implantable, but in either case it is connected through leads to the patient's heart.

The dual chamber pacemaker of the present invention possesses five basic components in addition to the necessary power supply and leads for conducting electrical signals between the patient's heart and the pacemaker pulse generator. These components are an atrial sense amplifier, a ventricular sense amplifier, an atrial output stage, a ventricular output stage, and a digital controller circuit possessing programmable memory and logic circuits which time the production of atrial and/or ventricular stimulating output pulses as a function of the P-waves sensed by the atrial sense amplifier, R-waves sensed by the ventricular sense amplifier, parameter and mode data stored within the memory, the status of the power source voltage, and the condition of a reed switch which may be effected by an external magnetic field. It is contemplated that in the preferred embodiment of this invention, the pulse generator would be contained within a sealed metallic container electrically connected to the output stages to act as an indifferent electrode and a pair of output connectors or terminals adapted to be coupled by way of leads from the output terminals extending to the atrium and ventricle of the patient's heart.

If is further contemplated that the dual chamber pacemaker of the present invention may automatically operate in several different pacing modes depending on the presence or absence of sensed atrial and/or ventricular depolarizations, that is P-waves and/or R-waves, in a manner described generally, for example, in the aforementioned U.S. Pat. No. 4,312,355. In this context, it is contemplated that several modes of operation may automatically take place depending on the condition of the patient's heart.

Generally, if neither P-waves nor R-waves are present in the atrial and ventricular escape intervals set by the timing circuitry of the pacemaker, it will function in the dual chamber, A-V sequential fixed rate mode (DOO mode as this mode and others referred to herein are designated in the Report of the Inter-Society Commision for Heart Disease Resources in *Circulation*, Vol. L., October, 1974.) If P-waves are not present, but R-waves recur from time to time within the A-V delay interval, the device operates in the A-V sequential demand or DVI mode. If P-waves are present, this device operates in the atrial synchronous or VAT mode in the absence of R-waves sensed within the A-V escape interval or in the atrial synchronous ventricular inhibited (ASVIP) or VDT/I mode when R-waves recur within the A-V interval.

In addition, it is contemplated that the dual chamber pacemaker of the present invention may be externally programmed to operate in a number of different modes including: the fully automatic dual chamber, or DDD mode described above, in which the atrial and ventricular sense amplifiers and the atrial and ventricular output stages are fully operational; in the atrial-ventricular sequential pacing mode, or DVI mode, wherein atrial and ventricular stimulating pulses are provided in timed relationship to one another in the absence of sensed ventricular depolarizations; in the atrial synchronous, ventricular inhbited (ASVIP) mode, or the VDT/I mode, wherein the sensed atrial depolarizations cause the pulse generator to deliver a ventricular stimulation pulse unless a spontaneous or conducted ventricular depolarization is detected by the ventricular sense amplifier prior to the timing out of a suitable A-V delay period; or the ventricular demand pacing mode, the VVI mode, wherein the atrial sense amplifier and atrial output stages are not employed.

In addition it is contemplated that the pulse generator can be programmed to operate in the atrial asynchronous mode (AOO), the ventricular asynchronous mode (VOO), or the atrial and ventricular asynchronous modes (DOO), by selectively programming atrial and/or ventricular pulse widths to zero and sensitivity to infinite to arrive at the resulting combination.

Turning now to FIG. 1, there is shown an atrial sense amplifier 10, ventricular sense amplifier 12, atrial output stage 14, ventricular output stage 16, digital control and logic circuit 18, and three further circuits, the reed switch RF modulator circuit 20 for receiving remotely applied programming signals and magnetic field test signals, a crystal oscillator 22 for providing the basic clock frequency for the digital control and logic circuit 18, and a voltage controlled oscillator (VCO) circuit 24 for timing certain operations of the digital control and logic circuit 18. The atrial sense amplifier 10 is coupled between the atrial lead terminal 26 and the pulse generator case terminal 28 for sensing atrial depolarizations or P-waves and producing the atrial sense signals PAO. The ventricular sense amplifier 12 is similarly coupled to the case terminal 28 and the ventricular pacing lead terminal 30, for sensing ventricular depolarizations or R-waves and producing the ventricular sense signals RAO.

The digital control and logic circuit 18 is coupled to the output terminals of the atrial and ventricular sense amplifiers to receive the atrial amplifier output signal and the ventricular amplifier output signal, to process the signal in accordance with the mode to which the pacemaker is programmed and the parameters of atrial and ventricular timing escape intervals, and to produce, if appropriate, atrial pace initiate PWA signals and ventricular pace initiate signals PWV which are respectively coupled to input terminals of the atrial output stage 14 and the ventricular output stage 16 to initiate respective atrial and ventricular stimulating pulses. The production of the atrial and/or ventricular initiate pulses is dependent upon the presence or absence of sensed atrial and/or ventricular depolarizations of the heart within certain escape intervals established by the parameter data stored in memory within the digital control and logic circuit 18 and dependent upon whether or not the reed switch (circuit 20) is open or closed by the application of an external magnet or on the condition of an interference detector (not shown) within the ventricular sense amplifier 12 which responds to noise signals picked up by the ventricular sense amplifier. Ignoring for the moment the possibility of the closure of the reed switch or interference, and turning to the operation of the circuit in the DDD mode, the pulse generator will pace at a programmable lower rate if neither P-waves nor R-waves are sensed within the escape intervals established by lower rate data stored in memory. The A-V interval between the production of atrial and ventricular initiate signals by the digital control and logic circuit 18 is similarly programmable and, under these conditions, the total operation of the pacemaker is characterized as A-V sequential demand pacing.

If a P-wave is sensed by the atrial sense amplifier 10 within the programmed atrial escape interval, (corresponding to a programmable lower rate), the digital control and logic circuit 18 will not produce an atrial pace initiate signal, but instead will commence the timing of the A-V interval. If an R-wave is sensed by the ventricular sense amplifier 12 prior to the expiration of the A-V interval, the ventricular pacing initiate signal is similarly not produced, and all timing intervals will be reset. But if an R-wave is not sensed prior to the completion of the A-V interval, a ventricular pace initiate pulse will be provided by the digitial control and logic circuit to initiate the production of a ventricular pacing stimulus at the end of the delay.

If the memory within the digital control and logic circuit 18 is programmed to the VVI mode, the atrial sense amplifier output signal is ignored, and the atrial output initiate signal is not produced. Thus, the digital control and logic circuit 18 responds only to R-waves sensed by the ventricular amplifier 12 and produces only ventricular pace initiate signals in the absence of an R-wave occurring prior to the expiration of the ventricular escape interval.

If the device is programmed in the DVI mode, the atrial output signal of the atrial sense amplifier 10 is similarly ignored. However, the atrial output stage and the ventricular output stage received atrial and ventricular pace initiate signals at the programmable lower rate and separated by the A-V interval. If an R-wave is sensed during the escape interval and following the refractory period of the ventricular sense amplifier, the lower rate timing is reset. If an R-wave is sensed prior to the completion of the A-V interval and following the delivery of an atrial stimulating pulse to the heart, then the ventricular pace initiate signal is inhibited or not delivered and the lower rate escape interval is again reset.

In the atrial synchronous ventricular inhibited, or VDT/I mode, P-waves recurring at a rate exceeding the programmable lower rate, are sensed by the atrial sense amplifier and processed by the digital control and logic circuit 18 to commence the A-V timing interval. Again, if an R-wave is sensed prior to the completion of the A-V interval, the ventricular pacing output is inhibited and all timing circuits will be reset. But, if an R-wave is not sensed prior to the completion of the A-V interval, a ventricular pacing stimulus will be provided in response to a ventricular pace initiate signal at the end of the A-V interval. A sensed R-wave occurring within the programmed lower rate escape interval and after the refractory period since the last ventricular depolarization or stimulating pulse, will be processed by the digital control and logic circuit 18 to restart the lower rate timing interval.

The above modes of operation may be selected by the physician to conform the operation of the pacemaker to the patient's condition or the condition of the atrial or ventricular pacing leads. Ordinarily it would be expected that the pacemaker would be left operating in the fully automatic dual chamber or DDD mode, with the lower rate interval, A-V timing interval and other parameters of operation of the device being selected and programmed to conform to the patient's condition.

FIG. 1 also indicates a diagrammatic representation of the patient's heart. A lead 33 extends to the atrium or upper chamber of the heart, and lead 33 has an electrode 36 which contracts the heart at the atrium. Similarly, lead 34 extends to the ventricle or lower chamber of the heart, and it has an electrode 38 at its end which is in contact with the heart at the ventricle. Although two separate leads 33 and 34 are shown, a single multiple conductor lead having separate electrodes at its tip and at a point along its side may be used for contact with the ventricle and atrium, as is generally known in the art. Leads 33 and 34 connect respectively to terminals 26 and 30 provided on the connector of the pulse generator for connection to the various electrical components and circuits within the pulse generator. An indifferent electrode 28, which may be the pulse generator case, is connected to terminal 40 and the various circuits shown in FIG. 1.

The pulse generator as described above conforms to that shown and further described in commonly assigned copending U.S. patent application Ser. No. 235,069, filed Feb. 17, 1981, in my name, which application is hereby incorporated herein by reference.

Figure 2:
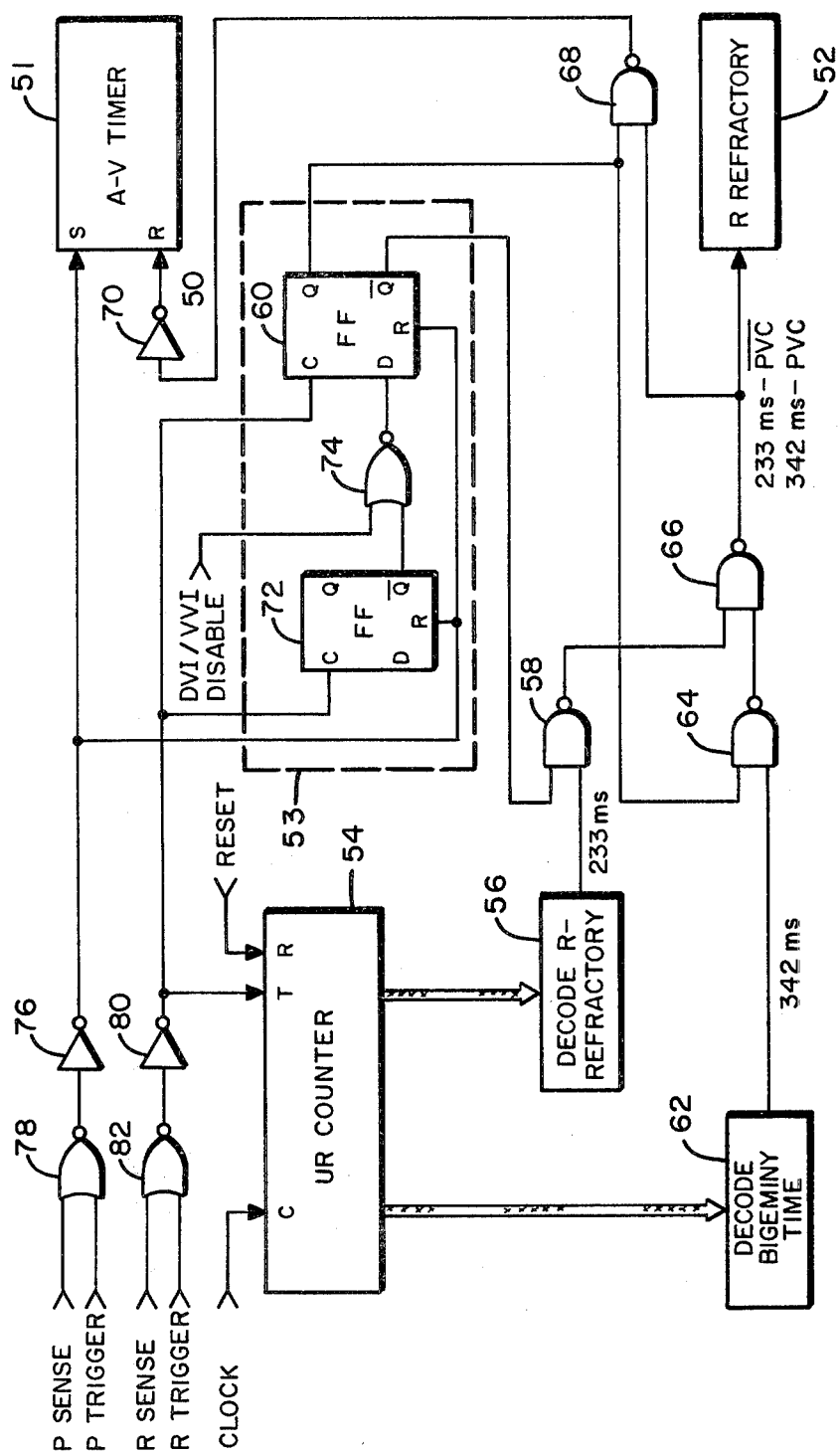
FIG. 2 is a block diagram of the preferred embodiment of the circuit for effecting the A-V interval prolongation of the present invention.

Turning now to FIG. 2 there is depicted the circuit within the digital controller and programmable memory 18 in FIG. 1 which according to the present invention develops at terminal 50 an A-V disable interval signal which, when applied to the A-V timer 51 disables the A-V timer 51 for a certain "bigeminy" time upon the counting of two or more successive R-waves, e.g. an ectopic ventricular contraction following a ventricular stimulation, without either the sensing or production of an intervening atrial depolarization by the counter 53. In addition, the circuit of FIG. 2 provides for a ventricular sense amplifier refractory signal at the refractory circuit 52 which is either the normal refractory period which follows the detection or production of a ventricular depolarization or an extended refractory period which follows the detection of an ectopic ventricular depolarization. Preferably, the bigeminy time period and the extended refractory time period are 342 ms and the normal ventricular refractory period is 233 ms. The refractory circuit 52 prevents the lower rate timer (not shown) that determines the pacing rate from being reset.

The upper rate counter 54, the ventricular refractory circuit 52 and the ventricular refractory decoding circuit 56 are described in greater detail in the aforementioned U.S. patent application Ser. No. 235,069. It will be understood, as described in that incorporated application, that the upper rate counter 54 is incremented by clock impulses whenever a ventricular depolarization is detected or a ventricular trigger impulse is provided and is reset upon achievement of its upper rate count.

The ventricular refractory period decoding circuit 56 is a logic circuit for decoding a first count of counter 54 and provides a signal, representing the control of time between the sensing or triggering of a ventricular depolarizations and the achievement of the first count, which is applied to one input terminal of NAND gate 58. The second input of NAND gate 58 is coupled to the $\overline{Q}$ output of data flip-flop 60.

The bigeminy time decoding circuit 62 is a further logic circuit for decoding a second count of counter 54 and provides a further signal representing the interval of time between the sensing or triggering of a ventricular depolarization and the achievement of the second count, preferably an interval of 342 ms. The output signal of the bigeminy time decoding circuit 62 is coupled to one input terminal of NAND gate 64. The other input terminal of NAND gate 64 is coupled to the Q output of flip-flop 60. The NAND gates 58, 64 and 66 present either the normal ventricular refractory interval decoded by the ventricular refractory decoding circuit 56 or the bigeminy time interval of the bigeminy timed decoding circuit 62 at the output terminal 52, depending on the logic state of the flip-flop 60. Similarly, the NAND gate 68 and inverter 70 present the 342 ms bigeminy time interval at the terminal 50, depending on the state of the flip-flop 60 in order to disable the A-V timer 51 for the 342 ms interval when the Q output of flip-flop 60 is high. The A-V timer 51 is started by a P-sense or P-trigger signal, at its set input.

The counter 53 for counting ventricular events comprises the flip-flops 60 and 72 and NOR gate 74. The clock and data inputs C and D of flip-flop 60 are respectively coupled to the clock input of flip-flop 72 and to the output of NOR gate 74. A reset input R of flip-flop 60 is coupled to the reset input of flip-flop 72 and to the output of inverter 76. The inverter 76 is coupled to the NOR gate 78 which has its inputs coupled to the atrial sense (P-sense) and atrial trigger (P-trigger) signals developed within the digital controller and programmable memory 18. Similarly, the clock inputs of flip-flops 72 and 60 are coupled to the output of inverter 80 which, in turn, is coupled to the output of NOR gate 82. The inputs of NOR gate 82 are coupled to the ventricular sense (R-sense) and the ventricular trigger (R-trigger) input signals developed within the digital controller and programmable memory 18. In general, a P-trigger or R-trigger signal is developed at a time shortly before (such as two clock cycles) the development of an atrial output initiate pulse and a ventricular output initiate pulse, respectively. The P-sense and R-sense signals are developed by the respective atrial and ventricular amplifiers 10 and 12. A further input of NOR gate 74 is coupled to receive a DVI/VVI disable signal from the digital controller and programmable memory 18. This signal is normally a low logic level signal except when the atrial sense amplifier 10 is disabled (or its output is ignored), that is, when the pulse generator is programmed to operate in the DVI or VVI modes. The low logic level signal at one input arms NOR gate 74 to provide a high logic signal at its output only when the $\overline{Q}$ output of flip-flop 72 assumes a low logic level.

Figure 3:
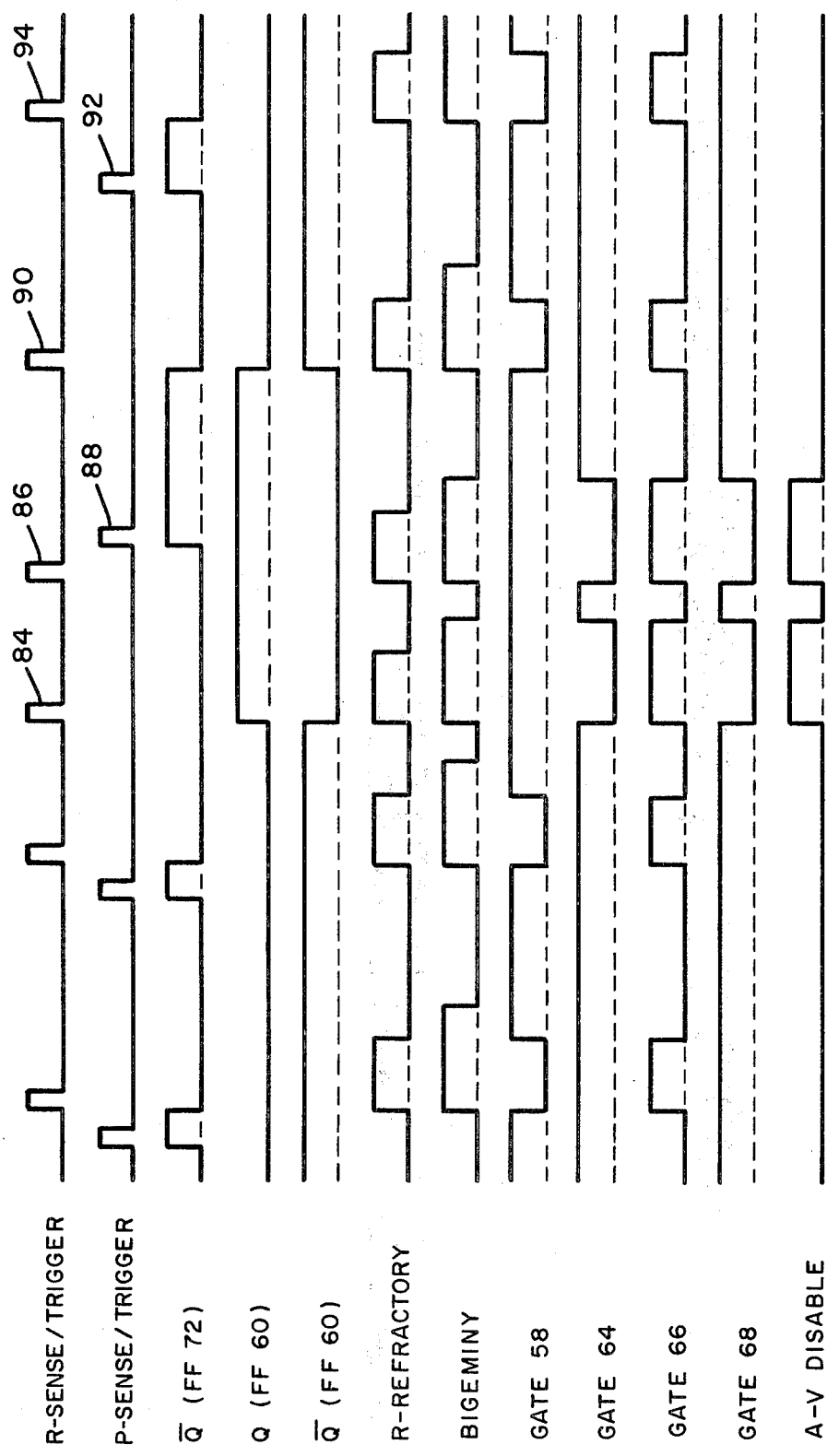
FIG. 3 is a graph of pertinent waveforms showing the operation of the circuit of FIG. 2.

Turning now to FIG. 3, there is depicted a waveform segment of operation of the circuit of FIG. 2. At the top of FIG. 3, the R-sense/trigger and P-sense/trigger impulses are depicted. It will be assumed that the signals, in fact, represent sensed events in all cases except for the R-trigger signals 90 and 94 which are triggered by the immediate preceding P-sense signals 88 and 92. In operation, the flip-flops 72 and 60 comprise a counter for counting occurrence of ventricular events without the presense of an intervening atrial event. In the absense of such a condition, the Q and $\overline{Q}$ outputs of flip-flop 60 are in the high and low logic level conditions, respectively. This insures that the NAND gate 68 cannot assume a low logic level condition regardless of the logic level state of its other input. The normally high output of gate 68 is inverted by inverter 70 to provide a low logic level condition at output terminal 50 under such normal conditions. Such a normal condition is depicted in the left-hand portion of FIG. 3 in the two bottom waveform diagrams which depict the output states of NAND gate 68 and inverter 70.

Under normal conditions, the logic levels of the Q and $\overline{Q}$ output of flip-flop 60 insure that the NAND gate 64 can only assume a high logic level at its output. The NAND gate 58 can, however, assume a low logic level at its output each time the high logic level ventricular refractory interval signal is developed by the ventricular refractory decoding circuit 56. Thus, the NAND gate 66 can produce at its output high logic level signals of a duration equal to the normal ventricular refractory period decoded by the ventricular refractory decoding circuit 56, or 233 ms, for example. That signal, when applied to one input of NAND gate 68 cannot affect the output condition of NAND gate 68 since its other input is kept at a low logic level. Thus, as long as the atrial sense amplifier signals precede the ventricular sense amplifier output signal or ventricular trigger signal, the normal refractory interval is developed at terminal 52 and the A-V counter is not disabled.

During this interval, each atrial sense/trigger signal reset (or set) the state of counters 72 and 60 so that their Q and $\overline{Q}$ outputs are at low and high logic levels, respectively. The clock inputs of flip-flops 72 and 60 receive the R-sense/trigger input signals, and flip-flop 72 is toggled by such conditions to switch its output state until it is again reset. The data or D input of flip-flop 60 is, however, at a low logic level at the time an R-sense/trigger signal is applied to its clock input, and consequently the flip-flop 60 remains with its Q output low and its $\overline{Q}$ output high.

Ventricular ectopic depolarizations are depicted in FIG. 3 as R-sense signals 84 and 86. R-sense signal 84 represents an ectopic ventricular depolarization which presumably occurred after the preceding ventricular refractory interval, but before the atrial depolarization or P-wave. Such a condition is referred to as a bigeminy condition in the patient's heart, occuring when a ventricular heart rate exceeds the atrial heart rate. Since the atrium may be ready to depolarize after delivery of the ventricular depolarization, it may be sensed and recommence the triggering of a ventricular depolarization after the present A-V interval. In such circumstances, it is desirable to prolong the A-V delay interval to insure that the delivered ventricular depolarization falls outside the heart's vulnerable period.

The R-sense signal 84 is applied to the clock inputs of flip-flops 72 and 60. Flip-flop 72 does not change its state in response to the clock input since it had previously been clocked by the preceding ventricular depolarization. At that instant, however, the flip-flop 60 changes state so that its Q and $\overline{Q}$ outputs are at high and low logic levels respectively. When that occurs, the NAND gate 68 is enabled by the high logic level of the Q output of flip-flop 60 to switch to a low logic level at its output upon the application of the next high logic level output signal of NAND gate 66. In addition, the logic levels applied to the NAND gates 64 and 58 by the Q and $\overline{Q}$ outputs respectively cause the gate 58 to assume a high logic level at its output regardless of the logic level condition at its other input. Thus, gate 64 may be switched to its low logic level at its output each time the bigeminy time is decoded by bigeminy decoding circuit 62. The low logic level output of gate 64 thus prevails for the 342 ms bigeminy time and, when applied to NAND gate 66 causes the production of corresponding 342 ms high logic level signal at terminal 52 and the further input of NAND gate 68. Thus, as shown in the third from last line of FIG. 3, the refractory intervals 233 ms are normally applied to the refractory circuit 52 until the bigeminy condition triggers the switching of flip-flop 60, whereupon the 342 ms bigeminy refractory interval is applied to circuit 52. Similarly, the 342 ms interval is applied to terminal 50 each time a ventricular depolarization (R-sense signals 84 and 88) occurs without an intervening P-wave. Thus, it can be seen that the circuit of FIG. 2 provides differing ventricular refractory intervals for normal and ectopic ventricular sensed events and provides for the extension of the A-V delay interval in response to sensed ventricular events.

The effect of the A-V delay is depicted in reference to P-sense signal 88 and the R-trigger signal 90. When the signal 88 is developed, the flip-flop 72 is reset, but the flip-flop 60 remains in its previously set condition due to the high logic level signal at its data input D. Thus, the 342 ms A-V disable signal is again produced. The subsequently delivered R-trigger signal 90 is delayed by the A-V disable interval and the normal delay interval programmed into memory in the digital controller and programmable memory 18. Thus, the R-trigger signal is delivered after the vulnerable period in the heart, due to the preceding ectopic ventricular depolarization signified by the R-sense signal 86.

If, however, an R-wave would have followed the P-trigger signal 88 within the underlying A-V time window, R-trigger pulse following the P-sense or P-trigger pulse reestablishes the conditions shown in FIG. 3 at the time of R-trigger signal 90.

The signals 92 and 94 represent P-sense and R-trigger events wherein the R-trigger follows the P-sense signal by the normal A-V delay.

The ventricular refractory interval is the time during which the pacemaker timing cannot be rest by ventricular amplifier outputs. The lengthened ventricular refractory period of 342 ms is developed as described above when no A-V interval is being timed out, that is on the occurrence of an ectopic depolarization. This insures that both the A-V interval (if any is initiated by a subsequent P-wave) and the ventricular refractory intervals are prolonged. The prolonged ventricular refractory interval is desirable since ectopic depolarizations tend to exhibit higher energy or longer lasting signals that can provide storing polarization voltage on the lead electrodes. This can lead to erroneous resetting of the ventricular sense amplifiers upon termination of the normal refractory period.

The invention may be implemented in any suitable analog or digital circuitry including software controlled custom or conventional microprocessors and the various timing intervals may be selectively programmed. These and other modifications or uses of the invention will be apparent to those skilled in the art.

I claim:
1. A pulse generator comprising:
   atrial and ventricular terminal means for connection respectively to the atrium and ventricle of a patient's heart;
   ventricular pulse providing means connected to said ventricular terminals means for selectively delivering stimulating pulses to said ventricular terminals means at a ventricular timing rate;
   atrial and ventricular sensing means connected to said atrial and ventricular terminal means and operative for sensing atrial and ventricular contractions of the patient's heart;
   atrial-ventricular (A-V) timing means operatively connected to said atrial sensing means and said ventricular pulse providing means and operative in response to a sensed atrial contraction to cause said ventricular pulse providing means to deliver a stimulating pulse at the end of a first A-V delay interval from said sensed atrial contraction;
   counting means for counting ventricular contractions and providing an A-V disable interval signal commencing when a ventricular contraction is sensed following a prior ventricular contraction and in the absence of an intervening atrial contraction; and means responsive to the A-V disable interval signal for preventing said A-V timing means from responding to a sensed atrial contraction for the duration of the A-V disable interval.

2. The pulse generator of claim 1 wherein said counting means further comprises:

first counting means for commencing a ventricular refractory interval signal and an A-V disable interval signal upon the sensing of a ventricular contraction;

second counting means for counting the number of ventricular contractions and providing a first gating signal when more than one ventricular stimulating pulse or contraction is sensed following a sensed atrial contraction and a second gating signal when an atrial contraction is sensed between each sensed ventricular contraction or stimulating pulse;

first gating means responsive to said first gating signal for providing said A-V disable signal to said preventing means to prolong said A-V time interval until the expiration of the A-V disable signal; and second gating means responsive to said second gating signal and said refractory interval signal for providing a refractory interval during which ventricular sense signals cannot reset the ventricular timing interval.

3. The pulse generator of claim 2 wherein said first counting means further comprises:

a counter triggered in timed relationship to a ventricular contraction or a ventricular stimulating pulse;

ventricular refractory count decoding means for providing a ventricular refractory count decoding means for providing a ventricular refractory interval signal when said counter reaches a first count; and A-V disable count decoding means for providing said A-V disable interval signal when said counter reaches a second count higher than said first count.

4. The pulse generator of claim 3 wherein said second gating means is further responsive to said first gating signal and said A-V disable interval signal for providing said A-V disable interval signal as a further refractory interval during which sensed ventricular contractions are not effective to reset the ventricular timing, said further refractory interval exceeding in length said refractory interval.

5. The pulse generator of claim 1 wherein said counting means further comprises:

a counter for counting the number of ventricular and atrial contractions and providing a first gating signal when a ventricular contraction follows a preceding ventricular stimulating pulse or contraction; and gating means responsive to said first gating signal for providing said A-V disable signal to said preventing means to prolong said A-V time interval until the expiration of the A-V disable signal.

6. The pulse generator of claim 5 wherein said counting means further comprises:

a further counter triggered in timed relationship to a ventricular contraction or a ventricular stimulating pulse;

ventricular refractory count decoding means for providing a ventricular refractory interval signal when said counter reaches a first count; and A-V disable count decoding means for providing said A-V disable interval signal when said counter reaches a second count higher than said first count.

7. The pulse generator of claim 6 wherein said counter provides a second gating signal when an atrial contraction occurs between each ventricular contraction or stimulating pulse; and further comprising:

further gating means responsive to said second gating signal and said refractory interval signal for providing a refractory interval during which sensed ventricular depolarizations are not effective to reset the ventricular timing interval.

8. The pulse generator of claim 6 wherein said further gating means is further responsive to said first gating signal and said A-V disable interval signal for providing said A-V disable interval signal as a further refractory interval during which sensed ventricular depolarizations are not effective to reset the ventricular timing, said further refractory interval exceeding in length said refractory interval.

9. An atrial and ventricular pulse generator comprising:

atrial sensing means for sensing atrial contractions of the heart and providing an atrial sense signal;

ventricular sensing means for sensing ventricular contractions of the heart and providing a ventricular sense signal;

atrial pulse providing means for providing atrial stimulating pulses in response to atrial trigger signals;

ventricular pulse providing means for providing ventricular stimulating pulses in response to ventricular trigger signals; and means responsive to atrial and ventricular sense signals and selectively providing atrial and ventricular trigger signals for triggering said atrial and ventricular pulse providing means at a predetermined lower rate timing interval further comprising:

atrial-ventricular (A-V) timing means responsive to an atrial sensing signal for commencing an A-V delay interval and providing a ventricular trigger signal upon the termination of the A-V delay interval;

first counting means for commencing an A-V disable interval signal upon the production of a ventricular sense signal;

second counting means for counting the number of ventricular and atrial sense signals and providing a gating signal when more than one ventricular sense signal occurs following an atrial sense signal; and gating means responsive to said gating signal for providing said A-V disable signal to said A-V delay interval timing means to prolong said A-V time interval until the expiration of the A-V disable signal.

10. The pulse generator of claim 9 wherein said first counting means further comprises:

a counter triggered in timed relationship to a ventricular sense or a ventricular trigger signal; ventricular refractory count decoding means for providing a ventricular refractory interval signal until said counter reaches a first count; and A-V disable count decoding means for providing said A-V disable interval signal until said counter reaches a second count higher than said first count;

said second counting means provides a second gating signal when an atrial sense signal occurs between each ventricular sense signal; and further comprising:
further gating means responsive to said second gating signal and said refractory interval signal for providing a refractory interval during which sensed ventricular depolarizations are not effective to reset the ventricular timing interval.

11. An atrial and ventricular pulse generator comprising:
atrial sensing means for sensing atrial contractions of the heart and providing an atrial sense signal;
ventricular sensing means for sensing ventricular contractions of the heart and providing a ventricular sense signal;
atrial pulse providing means for providing atrial stimulating pulses in response to an atrial trigger signal;
ventricular pulse providing means for providing ventricular stimulating pulses in response to ventricular trigger signal; and
means responsive to atrial and ventricular sense signals and selectively providing atrial and ventricular trigger signals for triggering said atrial and ventricular pulse providing means at a predetermined lower rate timing interval further comprising:
atrial-ventricular (A-V) timing means responsive to an atrial sensing signal for commencing an A-V delay interval and providing a ventricular trigger signal upon the termination of the A-V delay interval;

first counting means for commencing a ventricular refractory interval signal and an A-V disable interval signal upon the production of a ventricular sense signal;
second counting means for counting the number of ventricular and atrial sense signals and providing a first gating signal when more than one ventricular sense signal occurs following an atrial sense signal and a second gating signal when an atrial sense signal occurs between each ventricular sense signal;
first gating means responsive to said first gating signal for providing said A-V disable interval signal to said A-V delay interval timing means to prolong said A-V time interval until the expiration of the A-V disable interval signal; and
second gating means responsive to said second gating signal and said refractory interval signal for providing a refractory interval during which ventricular sense signals cannot reset the lower rate timing interval.

12. The pulse generator of claim 11 wherein said second gating means is further responsive to said first gating signal and said A-V disable interval signal for providing said A-V disable interval signal as a further refractory interval during which sensed ventricular depolarizations are not effective to reset the ventricular timing, said further refractory interval exceeding in length said refractory interval.

* * * * *

UNITED STATES PATENT AND TRADEMARK OFFICE
CERTIFICATE OF CORRECTION

PATENT NO. : 4,407,287
DATED : October 4, 1983
INVENTOR(S) : Lodewijk-Jozef Herpers It is certified that error appears in the above-identified patent and that said Letters Patent is hereby corrected as shown below:

Front page and column 1, the Title should read --Atrial And Ventricular And Ventricular-Only Pacemaker Responsive To Premature Ventricular Contractions--.

Column 8, line 10, insert --C-- between "input" and "of";
line 49, change the second "Q" to --$\overline{Q}$--.

Signed and Sealed this

Nineteenth Day of February 1985

[SEAL]

Attest:

DONALD J. QUIGG

Attesting Officer

Acting Commissioner of Patents and Trademarks